United States Patent
Pemberton et al.

(10) Patent No.: US 12,311,142 B2
(45) Date of Patent: May 27, 2025

(54) MEDICAL PIN INDEX RESIDUAL PRESSURE VALVE

(71) Applicant: The ESAB Group, Inc., North Bethesda, MD (US)

(72) Inventors: Gareth Pemberton, Worcester (GB); Karel Zmek, Chotebor (CZ); Zdenek Firych, Chotebor (CZ)

(73) Assignee: THE ESAB GROUP, INC., North Bethesda, MD (US)

( * ) Notice: Subject to any disclaimer, the term of this patent is extended or adjusted under 35 U.S.C. 154(b) by 34 days.

(21) Appl. No.: 18/347,654

(22) Filed: Jul. 6, 2023

(65) Prior Publication Data
US 2024/0358991 A1    Oct. 31, 2024

Related U.S. Application Data

(60) Provisional application No. 63/498,040, filed on Apr. 25, 2023.

(51) Int. Cl.
| F16K 15/06 | (2006.01) |
| A61M 39/24 | (2006.01) |
| F16K 27/02 | (2006.01) |

(52) U.S. Cl.
CPC .......... *A61M 39/24* (2013.01); *F16K 15/063* (2013.01); *F16K 27/0209* (2013.01)

(58) Field of Classification Search
CPC .... F16K 15/063; F16K 27/0209; A61M 39/24
See application file for complete search history.

(56) References Cited

U.S. PATENT DOCUMENTS

| 587,704 | A |  | 8/1897 | Clayton |
| 4,402,340 | A |  | 9/1983 | Lockwood, Jr. |
| 5,282,493 | A |  | 2/1994 | Schwartz et al. |
| 5,704,589 | A |  | 1/1998 | Canuteson |
| 7,320,334 | B1 | * | 1/2008 | Trimble .............. F15B 11/0445 137/493.1 |
| 9,297,373 | B2 | * | 3/2016 | Bagagli ................. F16K 17/044 |
| 10,024,439 | B2 |  | 7/2018 | Young et al. |
| 11,118,737 | B2 |  | 9/2021 | Stephan et al. |

(Continued)

FOREIGN PATENT DOCUMENTS

| DE | 60121505 T2 | 3/2007 |
| EP | 0458253 B1 | 2/1995 |
| FR | 2955170 A1 | 7/2011 |

(Continued)

OTHER PUBLICATIONS

Notification of Transmittal of International Search Report and Written Opinion including International Search Report and Written Opinion for International Application No. PCT/US2024/024552 mailed Jul. 26, 2024, 17 pages.

*Primary Examiner* — P. Macade Nichols
(74) *Attorney, Agent, or Firm* — Edell, Shapiro & Finnan, LLC (57) ABSTRACT

A medical pin index valve includes a pair of pin holes, the positions of which are selected based on the particular gas to be used with the pin index valve. The pin index valve includes a residual pressure device therein. In one embodiment, the residual pressure device is designed so that it closes the valve when the pressure in the tank is between 0.5 bar to 5 bar.

19 Claims, 9 Drawing Sheets

(56) References Cited

U.S. PATENT DOCUMENTS

2007/0215220 A1  9/2007  Bannon

FOREIGN PATENT DOCUMENTS

| FR | 2970058 A1 | 7/2012 |
| LU | 88212 A1 | 5/1993 |
| WO | 1999027282 A1 | 6/1999 |
| WO | 2013072372 A1 | 5/2013 |

* cited by examiner

MEDICAL PIN INDEX RESIDUAL PRESSURE VALVE

CROSS-REFERENCE TO RELATED APPLICATION

This application claims priority to and the benefit of U.S. Provisional Patent Application No. 63/498,040, entitled "MEDICAL PIN INDEX RESIDUAL PRESSURE VALVE," filed Apr. 25, 2023, the entire disclosure of which is incorporated herein by reference in its entirety for all purposes.

TECHNICAL FIELD

The present disclosure relates to a medical pin index valve and, more specifically, to a medical pin index valve that has a residual pressure device.

BACKGROUND

Pin index valves and used for various common inlet connections to tanks containing a fluid, such as a gas. In some instances, pin index valves are used with medical gases, such as Oxygen, Nitrous Oxide, Carbon Dioxide, air, and Entonox. Medical gas pin index valves typically have highly compact designs, which do not permit many parts or components to be contained therein.

Pressure tanks containing a gas are used and refilled. A pressure tank is more difficult to refill when it has been completely emptied. In addition, an empty pressure tank needs to be cleaned before it is refilled, thereby adding to the length of time it takes to refill a tank and use it for a subsequent process.

Current solutions have a few problems or challenges. One problem is the limited space in a pin index valve for any type of residual pressure device. Another problem is that the use of a spring in a residual pressure device has stability issues, sometimes caused by vibration of the spring during use of the valve. Another challenge is the material used in the single spring in a residual pressure device. Only stainless steel material can be used for in the implementation of a single spring, which is not a solution for Oxygen. If Inconel or Phosphorus Bronze or Beryllium Copper is used as the spring material, those springs are not stable in this size. The repeated compression of such springs renders them unstable at this length.

There is a need for a residual pressure device in a pin index valve. There is also a need for a compact residual pressure device in a pin index valve that can achieve a desired residual pressure in a tank to which the pin index valve is connected.

SUMMARY

The present invention relates to a medical pin index valve. The medical pin index valve includes a pair of pin holes, the positions of which are selected based on the particular gas to be used with the pin index valve. The pin index valve includes a residual pressure device therein. In one embodiment, the residual pressure device is designed so that it closes the valve when the pressure in the tank is between 0.5 bar to 5 bar.

The present invention relates to a pin index valve with a residual pressure device that includes a nested biasing mechanism or device. In one embodiment, the nested biasing mechanism includes a dual spring system. The dual spring system includes two different sized springs. One spring has a smaller diameter than the other spring. The smaller diameter spring is nested in the larger diameter spring. In addition, the smaller diameter spring has a longer length than the larger diameter spring.

The use of two springs creates the effect of a much stiffer spring in less than half the space it would take for a single spring that provide the same amount of biasing force. Each of the inner spring and the outer spring functions independently of the other spring. However, both of the inner and outer springs provide biasing forces in the same directions on the same components within the pin index valve. As a result, the springs have a cumulative biasing effect on the pin index valve components. By sitting the smaller diameter inner spring within the larger diameter outer spring, the inner spring is guided so that it meets lifetime operation requirements (150,000 cycles) and has a correct travel path.

The nested biasing mechanism functions as a residual pressure device within a medical pin index valve. In one embodiment, the nested biasing mechanism operates at a 0.5 bar to 5 bar residual pressure value in the tank to which the medical pin index valve is connected. By ensuring that 0.5 bar to 5 bar of gas remains in the tank, and that the tank is not emptied or the pressure in the tank is not reduced to the level of 1 bar, the residual pressure device according to the present invention provides protection against contamination in the tank, and also enables faster and more efficient filing of the cylinder. A single spring in a medical pin index valve would not be able to achieve the 0.5 bar to 5 bar residual pressure value. In one embodiment, the nested biasing mechanism may operate within a 3.0 bar to 4.0 bar range, which is a tighter tolerance than a single spring. This range results from being able to select a tighter k factor tolerance.

The two or more spring solution, referred to as nested configuration since at least one of the springs has to be located within another spring, achieves the desired residual pressure in a tank. In addition, stainless steel can be used with the springs in the nested biasing mechanism according to the present invention.

In an embodiment according to the present invention, a medical gas pin index valve comprises a body defining an inlet passageway, a body cavity, and an outlet passageway, the cavity being in fluidic communication with each of the inlet passageway and the outlet passageway, a fixed member coupled to the body, the fixed member being substantially located in the body cavity, the fixed member defining its own cavity, and a sealing member located in the fixed member cavity, the sealing member being placeable in a sealed position and an opened position, the sealing member preventing a fluid, such as a gas, from traveling from the inlet passageway to the outlet passageway when the sealing member is in its sealed position, the sealing member being biased toward its sealed position by a first spring and by a second spring, each of the first spring and the second spring engaging both the fixed member and the sealing member, the second spring being located inside of the first spring.

In one embodiment, the sealing member moves to its sealed position when the pressure of a combined biasing force from the first spring and the second spring on the sealing member is greater than the pressure of the fluid in the inlet passageway. In another embodiment, the first spring has a first length, the second spring has a second length, and the second length is greater than the first length.

In yet another embodiment, the fixed member includes an inner end surface, the first spring engages a first portion of the inner end surface, the second spring engages a second portion of the inner end surface, and the second portion of the inner end surface is separated from the first portion of the inner end surface by an annular shoulder. In addition, the first spring engages a third surface on the sealing member, the second spring engages a fourth surface on the sealing member, and the fourth surface is different from the third surface.

In another embodiment, the sealing member includes a body that has an end surface and a cavity that has an inner end surface, the first spring engages the sealing member body end surface, and the second spring engages the sealing member body inner end surface. Alternatively, the sealing member body cavity is defined by an inner wall having a first diameter, the first spring has a second diameter, the second spring has a third diameter, the third diameter is smaller than the first diameter, and the first diameter is smaller than the second diameter. In yet another embodiment, the first spring has a first diameter and a first length, the second spring has a second diameter and a second length, the first diameter being greater than the second diameter, the first length being less than the second length, and each of the first spring and the second spring applies a simultaneous force on the sealing member to move the sealing member to its sealed position.

In another embodiment according to the present invention, a medical gas pin index valve comprises a body defining an inlet passageway and an outlet passageway, the body having a fixed member coupled thereto, the fixed member defining a first cavity, a sealing member movably mounted in the body, a least a portion of the sealing member being located in the first cavity, the sealing member defining a second cavity, the sealing member being placeable in a sealed position in which a fluid is prevented from traveling from the inlet passageway to the outlet passageway, and an opened position in which a fluid can travel from the inlet passageway to the outlet passageway, a first spring engaging the fixed member and the sealing member, the first spring biasing the sealing member toward its sealed position, and a second spring engaging the fixed member and the sealing member, the second spring biasing the sealing member toward its sealed position, wherein the first spring applies a first biasing force at a first location on the sealing member, and the second spring applies a second biasing force at a second location on the sealing member, the second location being located inside of the first location.

In one embodiment, a combination of the first biasing force and the second biasing force together moves the sealing member to its sealing position, thereby causing fluid having a residual pressure to remain in the inlet passageway. In another embodiment, the residual pressure is in the range of 0.5 bar to 4 bar. In yet another embodiment, the residual pressure is in the range of 3 bar to 4 bar.

In an alternative embodiment, the second spring is located inside of the first spring. In another embodiment, the first spring has a first diameter and a first length, the second spring has a second diameter and a second length, the first diameter is different than the second diameter, and the first length is different than the second length. In yet another embodiment, the first diameter is greater than the second diameter, the second length is greater than the first length, and the first spring and the second spring have a nested arrangement.

In another embodiment according to the present invention, a medical gas pin index valve comprises a valve body defining an inlet passageway, a cavity, and an outlet passageway, the body having a fixed member coupled thereto and located in the cavity, a sealing member movably mounted in the body, the sealing member being placeable in a sealed position in which a fluid is prevented from traveling from the inlet passageway to the outlet passageway, and an opened position in which a fluid can travel from the inlet passageway to the outlet passageway, and a nested biasing system located between the fixed member and the sealing member, the nested biasing system applying a first biasing force on the sealing member at a first location and a second biasing force on the sealing member at a second location, each of the first biasing force and the second biasing force being applied to the sealing member along a same direction, wherein the sealing member moves to its sealed position when the combination of the first biasing force and the second biasing force is greater than a pressure of a fluid in the inlet passageway.

In one embodiment, the nested biasing system includes a first spring engaging the fixed member and the sealing member, the first spring applying the first biasing force, and a second spring engaging the fixed member and the sealing member, the second spring applying the second biasing force, the second location being different than the first location. In another embodiment, the first spring has a first length, the second spring has a second length, the first length is less than the second length, and the second spring is located inside of the first spring.

In another embodiment, the sealing member includes a body that defines a cavity and that has an end surface outside of the cavity, the second location is inside the sealing member cavity, and the first location is on the sealing member end surface. In yet another embodiment, the biasing system applies a third biasing force on the fixed member in a second direction and a fourth biasing force on the sealing member on the fixed member in the second direction, and the third biasing force and the fourth biasing force are applied on the same surface of the fixed member.

BRIEF DESCRIPTION OF THE DRAWINGS

To complete the description and in order to provide for a better understanding, a set of drawings is provided. The drawings form an integral part of the description and illustrate embodiments of the present application, which should not be interpreted as restricting the scope of the application. The drawings include the following figures.

Like reference numerals have been used to identify like elements throughout this disclosure.

DETAILED DESCRIPTION

The following description is not to be taken in a limiting sense, but is given solely for the purpose of describing the broad principles of the present application. Embodiments of the present application will be described by way of example, with reference to the above-mentioned drawings showing elements and results of such embodiments.

Figure 1:
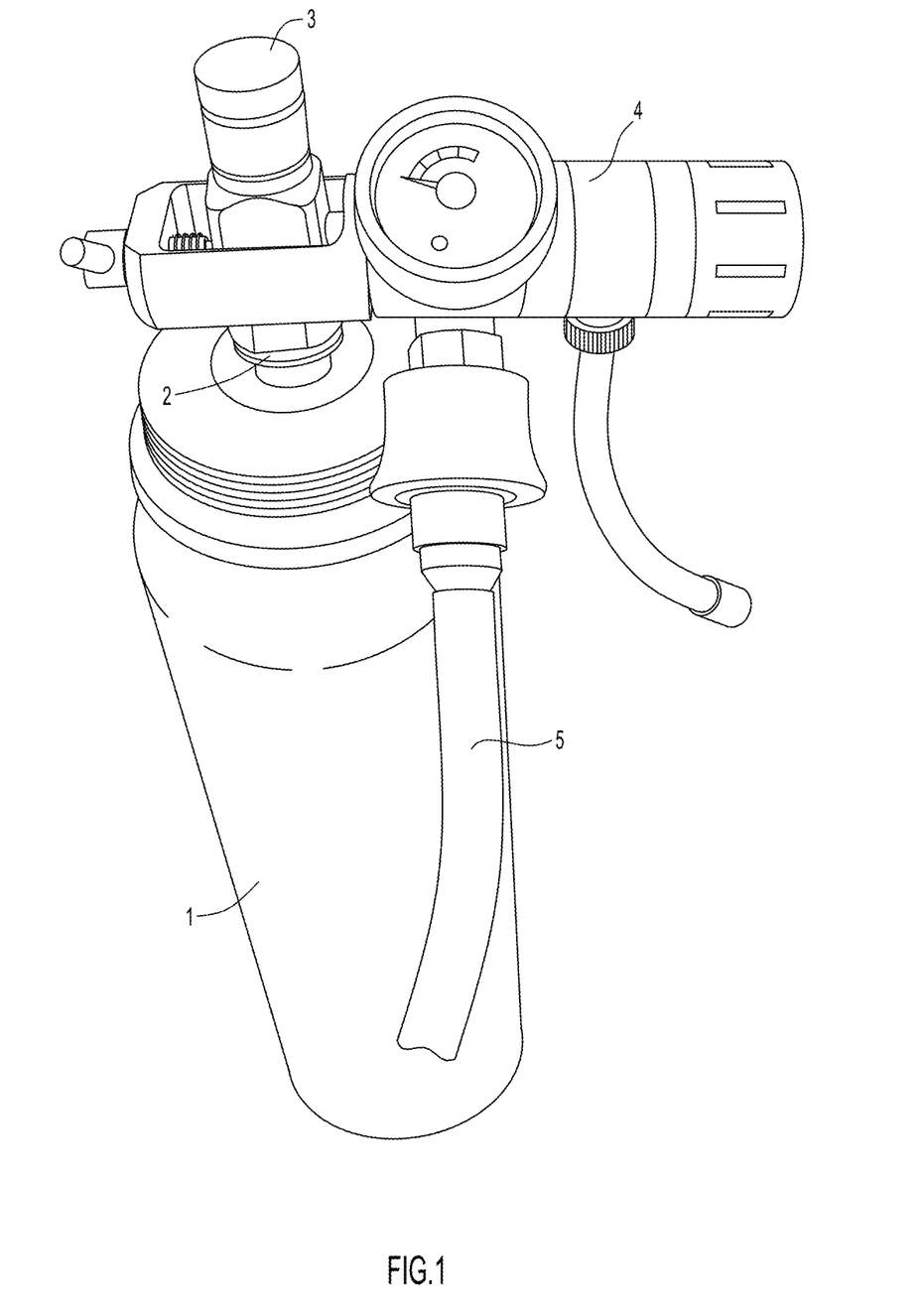
FIG. 1 is a perspective view of an embodiment of a medical pin index valve according to the present disclosure coupled to a pressurized gas tank.

Referring to FIG. 1, a perspective view of an embodiment of a medical pin index valve coupled to a pressurized gas tank is illustrated. In this embodiment, a medical pin index valve 3 is connectable with a pressurized gas tank 1 via connection 2. The tank 1 contains a pressurized gas that can be used in a variety of ways, some of which include medical purposes. Coupled to the medical pin index valve 3 is a volumetric flow regulator 4, which controls the flow of pressurized gas to gas connection 5.

Figure 2:
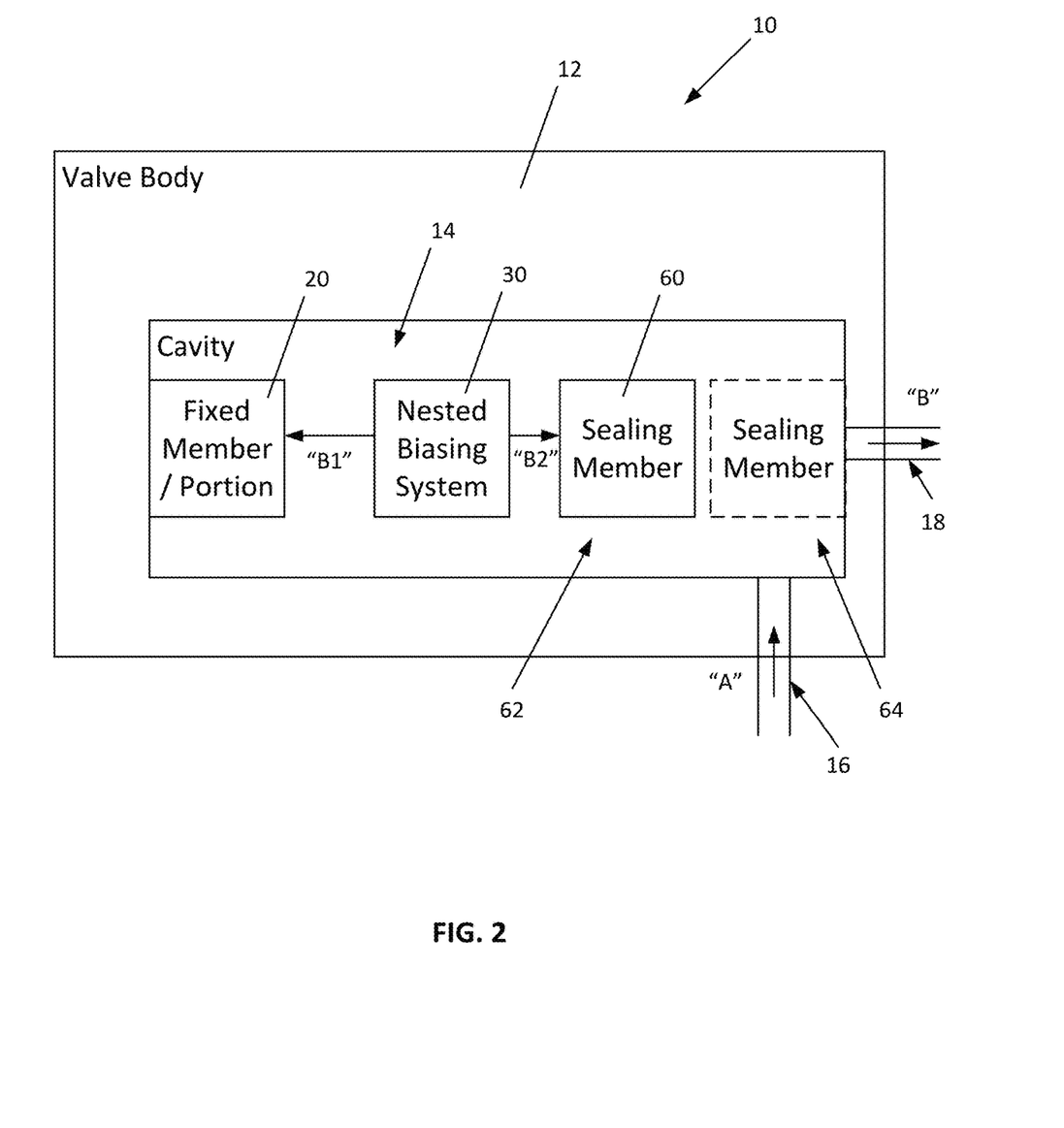
FIG. 2 is a schematic diagram of an embodiment of a medical pin index valve according to the present disclosure.

Referring to FIG. 2, a schematic diagram of an embodiment of a medical pin index valve according to the present disclosure is illustrated. In this embodiment, the medical pin index valve 10 includes a valve body 12 that defines a cavity 14 therein. The valve body 12 has an inlet or inlet passageway 16 and an outlet or outlet passageway 18, each of which is in fluidic communication with the cavity 14. Pressurized fluid flows through inlet passageway 16 along the direction of arrow "A" into the cavity 14 of the valve body 12. The pressurized fluid entering the inlet passageway 16 is from a gas source, such as a pressurized gas tank, to which the valve body 12 is connected. Pressurized fluid flows through outlet passageway 18 along the direction of arrow "B" from the cavity 14 of the valve body 12.

A fixed member or portion 20 is coupled to the valve body 12 so that the fixed member 20 does not move relative to the valve body 12. In one embodiment, the entire fixed member 20 is disposed in the cavity 14. In an alternative embodiment, only a portion of the fixed member 20 is disposed in the cavity 14.

The medical pin index valve 10 includes a movable or sealing member 60 that is located within the cavity 14 of the valve body 12. The sealing member 60 can move between an opened position 62 and a closed or sealed/sealing position 64 in the cavity 14. In its opened position 62, the sealing member 60 is spaced apart from the outlet passageway 18. As a result, pressurized fluid in the cavity 14 can flow along arrow "B" through outlet passageway 18 and exit the valve 10 for use in a medical process or procedure. In its sealed position 64, the sealing member 60 is proximate to the outlet passageway 18. In this position 64, the sealing member 60 seals the outlet passageway 18, thereby preventing pressurized fluid from exiting the cavity 14 and limiting any additional gas from an external gas source to enter the cavity 14.

In this embodiment, the medical pin index valve 10 includes a nested biasing system 30 which provides a residual pressure valve function. The nested biasing system 30 is located in the cavity 14. The nested biasing system 30 is located between the fixed member 20 and the sealing member 60. The nested biasing system 30 applies a biasing force on the fixed member 20 along the direction of arrow "B1." At the same time, the nested biasing system 30 applies a biasing force on the sealing member 60 along the direction of arrow "B2." In view of the fixed member 20 being secured in place, the nested biasing system 30 biases the sealing member 60 toward its sealing position 64.

The position of the sealing member 60 is determined by the relative forces applied to it. In this embodiment, one of the forces is the biasing force from the nested biasing system 30 along "B2" on the sealing member 60 and the pressurized gas force in inlet passageway 16 and cavity 14. When the magnitude of the biasing force along the direction of arrow "B2" is less than the pressurized gas force along the direction of arrow "A," the sealing member 60 moves from its sealing position 64 to an opened position 62, thereby opening the valve 10 and allowing pressurized gas to exit the cavity 14, which allows more gas to enter the cavity 14. When the magnitude of the biasing force along the direction of arrow "B2" is greater than the pressurized gas force along the direction of arrow "A," the sealing member 60 moves from its opened position 62 to its sealing position 64. The valve 10 closes and prevents pressurized gas from exiting the cavity 14.

The pressurized fluid entering the valve 10 through the inlet passageway 16 is from a pressurized gas source, such as a tank (see FIG. 1). As fluid leaves the pressurized gas source, the pressure inside of the gas source decreases. As a result, the force on the sealing member 60 along the direction of arrow "A" decreases. The pressurized gas from the gas source moves the sealing member 60 to its opened position 62, even as its pressure decreases. The pressurized gas maintains the sealing member 60 in an opened position 62 spaced from the inlet passageway 16 until the force of the gas along the direction of arrow "A" is less than the biasing force from the nested biasing system 30 along the direction of arrow "B2." Once the pressure of the pressurized gas drops lower than the biasing force from the nested biasing system 30, the sealing member 60 moves to its sealed position 64.

It is desirous to maintain a certain amount of pressurized gas in the gas source at the end of its use. The remaining or residual pressurized gas makes refilling the gas source easier and more efficient, and avoids the need to clean the gas source. According to the present invention, a residual pressure in the range of 0.5 bar to 5 bar remaining in the gas source is ideal, with 1.5 bar to 4 bar being preferable, and with 3 bar to 4 bar being more preferable. To achieve that residual pressure, the nested biasing system 30 needs to provide a very accurate biasing force "B2" on the sealing member 60 that is equivalent to the 0.5 bar to 5 bar range. In the very limited space in a cavity 14 of a medical pin index valve, the nested biasing system 30 has to be designed to provide that specified level of accurate force.

Figure 3:
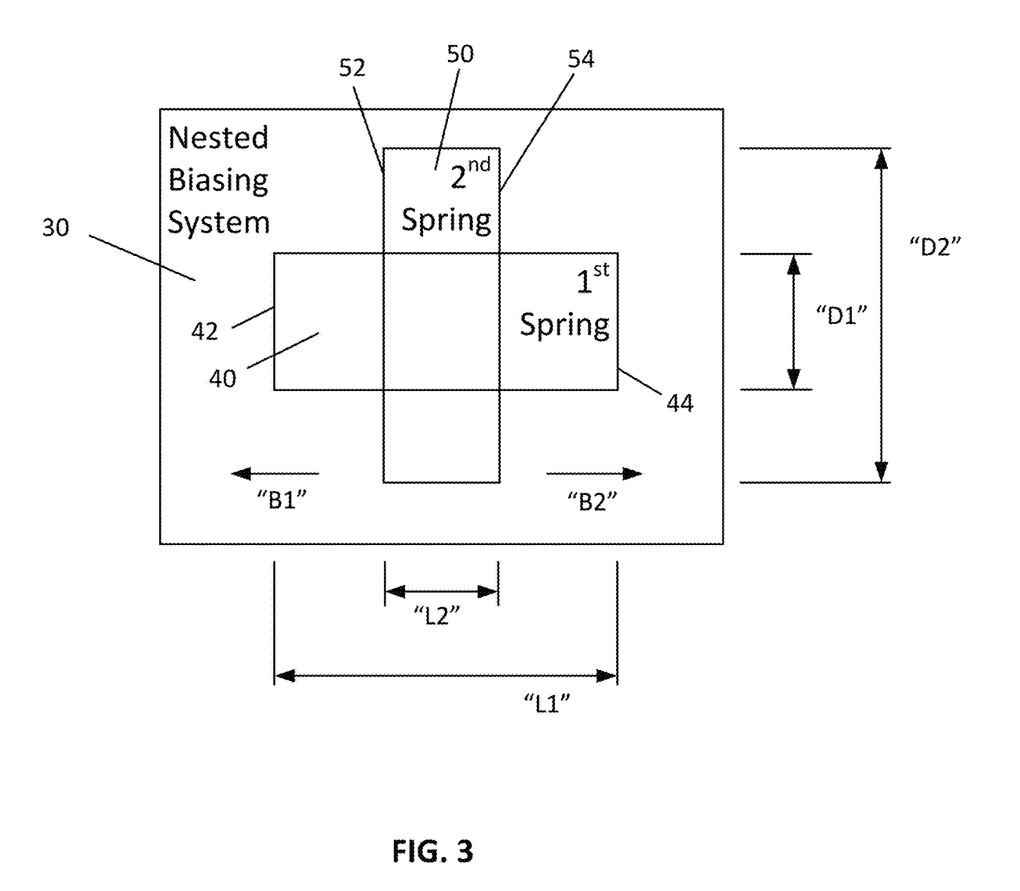
FIG. 3 is a schematic diagram of an embodiment of a nested biasing system according to the present disclosure.

Turning to FIG. 3, a schematic diagram of an embodiment of a nested biasing system according to the present disclosure is illustrated. In this embodiment, the nested biasing system 30 is a two spring system. In other embodiments, a third spring may be included as well. In this embodiment, the nested biasing system 30 includes a first spring 40 and a second spring 50. In FIG. 3, the first spring 40 and the second spring 50 are arranged in the cavity 14 in a nested arrangement in which one spring is inside of the other spring. While the terms "first" and "second" are used while describing FIG. 3, it is to be appreciated that either of the springs 40 and 50 can be referred to as the "first" spring and the other spring would be the "second" spring.

As shown, the first spring 40 has a first end 42 and an opposite second end 44. The length of the first spring 40 from end 42 to end 44 is represented by the arrow "L1." The first spring 40 has an outer diameter represented by the arrow "D1." Similarly, the second spring 50 has a first end 52 and an opposite second end 54. The length of the second spring 50 from end 52 to end 54 is represented by the arrow "L2." The second spring 50 has an outer diameter represented by the arrow "D2." In this embodiment, L1 is greater than L2, and D2 is greater than D1. Accordingly, the first spring 40 is longer than the second spring 50, but the first spring 40 has a smaller diameter than the second spring 50. As a result, the first spring 40 can be inserted into the second spring 50 and extend beyond both ends of the second spring 50.

The first spring 40 and the second spring 50 are oriented in the same direction. Thus, the first spring 40 biases a surface with end 42 along the direction of arrow "B1" and biases a surface with end 44 along the direction of arrow "B2." Similarly, the second spring 50 biases a surface with end 52 along the direction of arrow "B1" and biases a surface with end 54 along the direction of arrow "B2." The springs 40 and 50 apply biasing forces in the same directions as each other. Each of the springs 40 and 50 engages and applies a force on a surface of the fixed member 20 and the sealing member 60 at the same time as the other spring.

The net result is that the nested spring arrangement enables the fine tuning of the pressure of the nested biasing system 30 because two springs can be adjusted in terms of length, diameter, biasing force, etc. The opportunity to select two particular springs allows for the fine tuning of the biasing force applied by the nested biasing system 30, thereby enabling a pressure in the range of 0.5 bar to 5 bar to be achieved. In addition, the nested spring arrangement enables two springs to be used in the small cavity 14 of the valve body 10, which provides a better overall and more accurate pressure than a single spring in the cavity 14.

Figure 4:
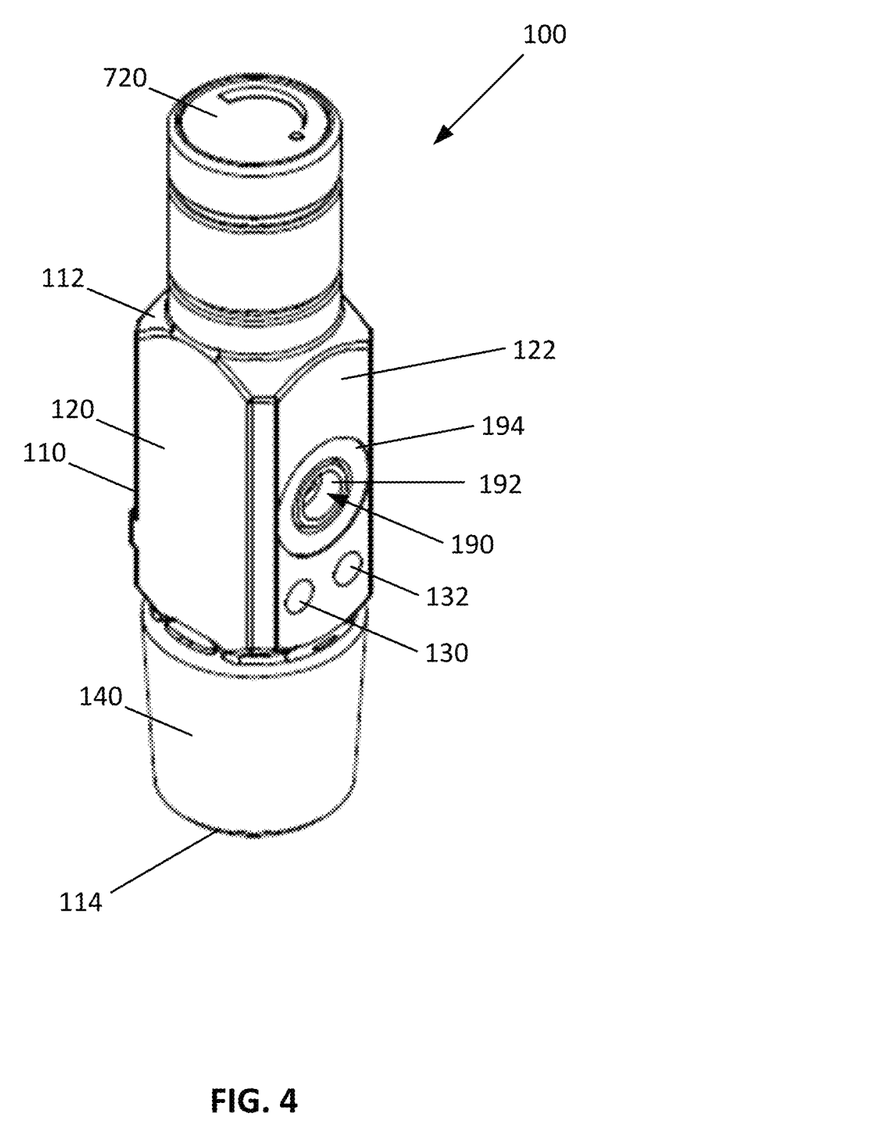
FIG. 4 is a perspective view of an embodiment of a medical pin index valve according to the present disclosure.
Figure 5:
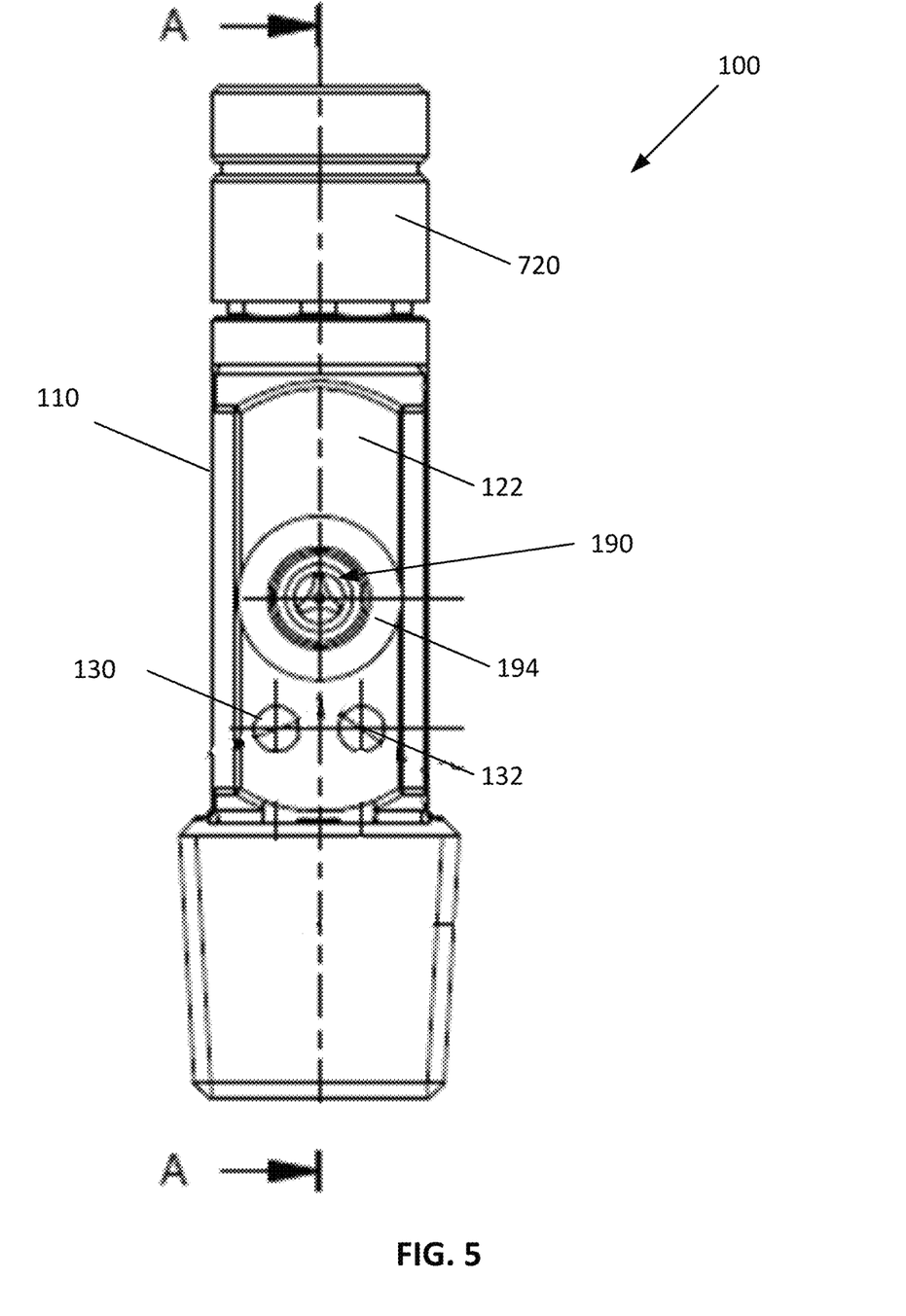
FIG. 5 is a side view of the medical pin index valve illustrated in FIG. 4.

Now an embodiment of a medical pin index valve according to the present disclosure is described. Turning initially to FIGS. 4 and 5, a perspective view and a side view, respectively, of medical pin index valve 100 are shown. In this embodiment, medical pin index valve 100 includes a body or valve body 110 that has an upper end 112 and an opposite lower end 114. The body 110 includes a main body portion 120 that has several side surfaces. One of the surfaces, 122, includes a pair of holes or openings 130 and 132 into which pins of a specific volumetric flow regulator may be inserted. The positions of the holes 130 and 132 are changed for different types of pressurized gases, thereby ensuring that the correct gas is being supplied through the valve. Also included on surface 122 is an outlet or outlet passageway 190 that is defined by a side wall 192. The outlet 190 has a groove 194 formed in the surface 122, which assists with the mating of another piece of equipment, such as a volumetric flow regulator, to the outlet 190. The body 110 also includes a lower portion 140 at one end and a handwheel 720 at the other end.

Figure 6:
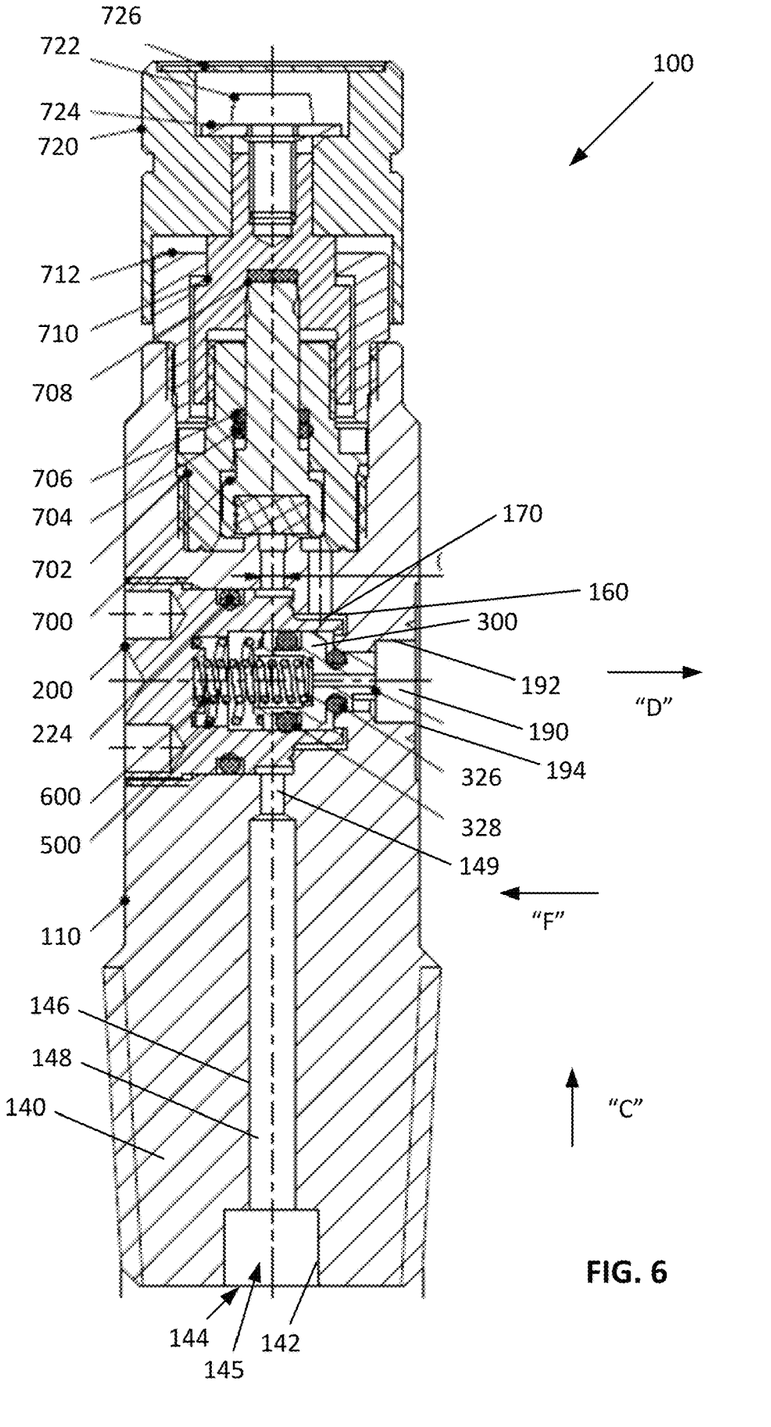
FIG. 6 is a cross-sectional side view of the medical pin index valve illustrated in FIG. 5 taken along line "A"-"A."

Referring to FIG. 6, a cross-sectional side view of the medical pin index valve 100 is taken along the line "A"-"A" in FIG. 5. In this view, several of the internal components of the valve 100 are shown. The lower portion 140 of the valve body 110 includes at the lower end an internal wall 142 that defines an opening 144 that forms the inlet or inlet passageway 145 into which pressurized gas flows into the valve body 110 from an external gas source, such as a pressurized gas tank. The inlet 145 includes a passageway portion or channel portion 148 that is defined by an inner wall 146. The diameter of the passageway is then reduced at section 149, which is adjacent to and in fluidic communication with body cavity 170, which is defined by several walls 160.

Pressurized gas can flow through inlet passageway 145 along the direction of arrow "C." When the pressurized gas enters the cavity 170, it applies a force on the internal components in the cavity 170 along the direction of arrow "F." If the magnitude of the pressure of the gas in inlet passageway 145 is sufficient, the pressurized gas will open the valve and flow into the cavity 170, as described in more detail below. The body 110 includes outlet passageway 190 through which gas from the cavity 170 can flow in the direction of arrow "D."

In the cavity 170 are a fixed member or portion 200 and a sealing member 300. Many of the details of fixed member 200 and sealing member 300 are discussed below relative to FIGS. 9 and 10. The fixed member 200 is located in the cavity 170, and the sealing member 300 is located in a cavity of the fixed member 200. Between the fixed member 200 and the sealing member 300 is a nested biasing system or mechanism. In this embodiment, the nested biasing system includes spring 500 and spring 600. As shown, spring 600 is longer than spring 500, and the outer diameter of spring 600 is smaller than the outer diameter of spring 500. As a result, spring 600 can be inserted into and pass through spring 500. Each of the springs 500 and 600 contacts the fixed member 200 and the sealing member 300.

To assist with sealing the fixed member 200 and the sealing member 300, an O-Ring 224 is located between the fixed member 200 and wall 160 of the cavity 170, an O-Ring 326 is located between the sealing member 300 and the wall 160, and a sealing member 328 is located between the sealing member 300 and the inner cavity wall of the fixed member 200.

Also shown in FIG. 6 are several other components of the valve 100. In this exemplary embodiment, the valve 100 includes a seat pin index 700, a gland 702, an O-Ring 704, and a back ring 706. A friction ring 708 is located adjacent to a spindle 710, around which a nut 712 is located. The handwheel 720 is coupled to the spindle 710 via a screw 722 and a washer 724 arrangement. A label 726 may be provided at the top of the handwheel 720.

Figures 7, 8:
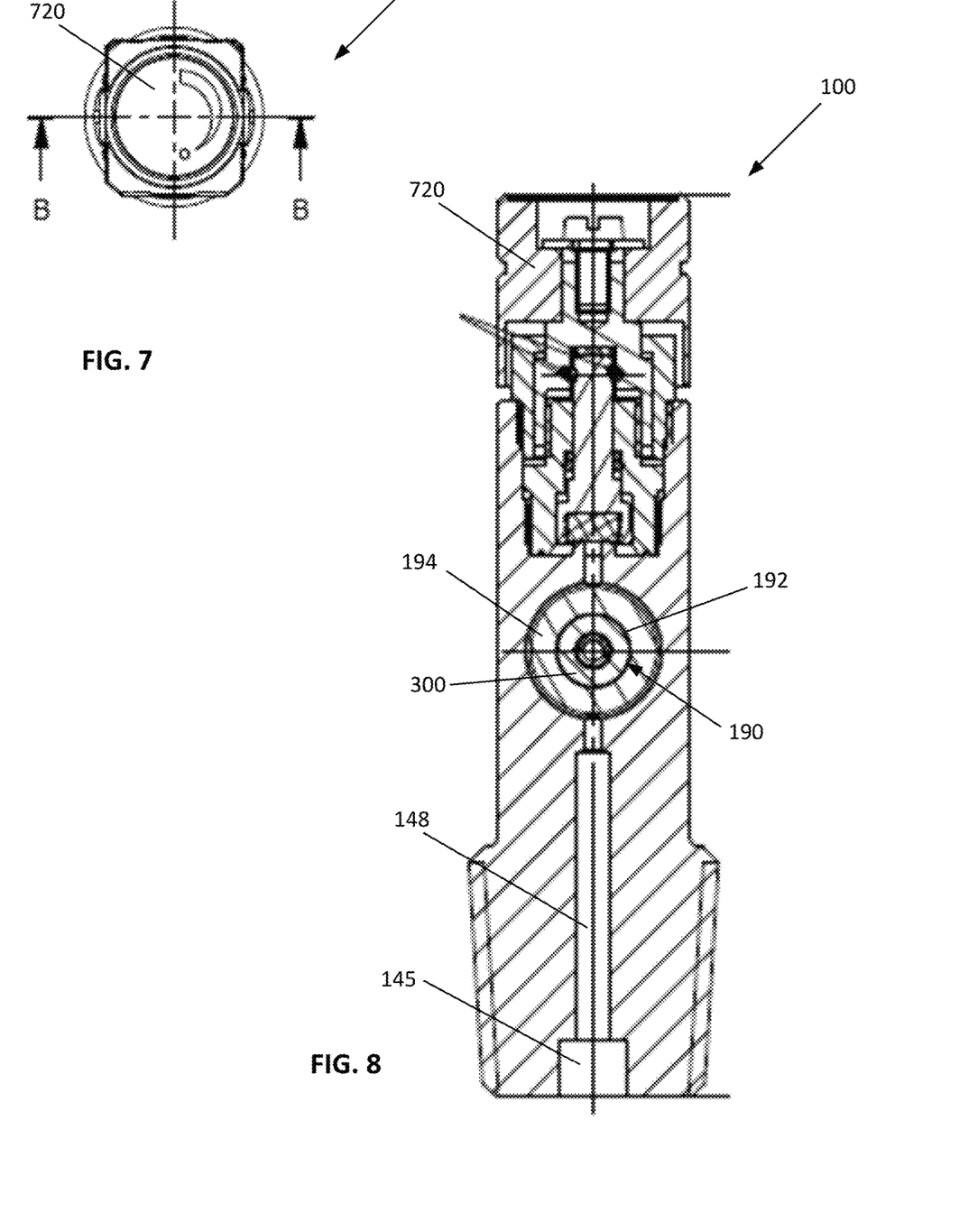
FIG. 7 is a top view of the medical pin index valve illustrated in FIG. 4.
FIG. 8 is a cross-sectional side view of the medical pin index valve illustrated in FIG. 7 taken along line "B"-"B."

Referring to FIGS. 7 and 8, a top view of the medical pin index valve 100 and a cross-sectional view taken along the line "B"-"B" in FIG. 7, respectively, are illustrated. The cross-sectional view in FIG. 8 is a different perspective than the cross-sectional view in FIG. 6. In FIG. 8, the sealing member 300 can be seen inside of the outlet 190. The groove 194 around the wall 192 is shown.

Figure 9:
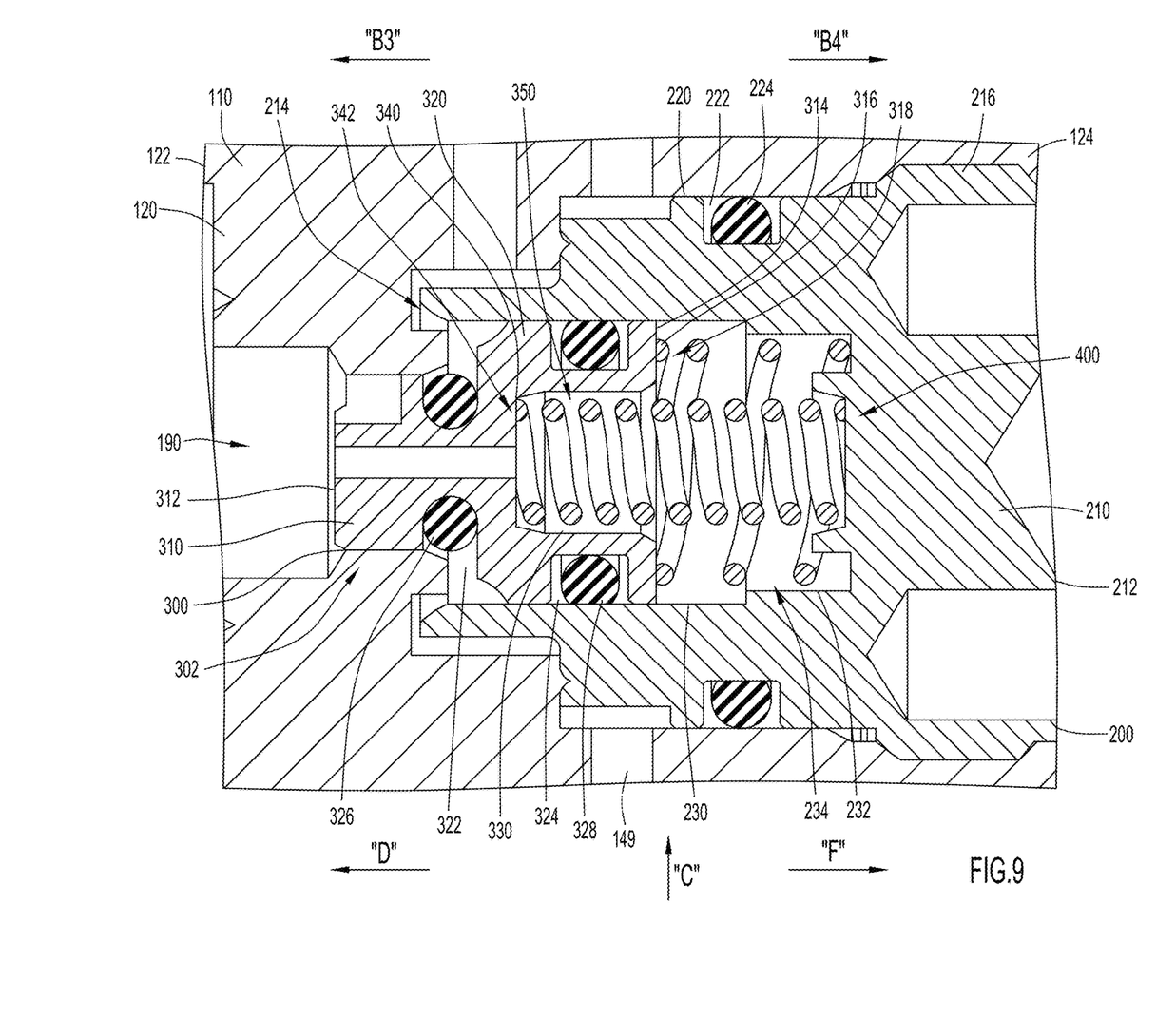
FIG. 9 is a close-up cross-sectional view of several components of the medical pin index valve illustrated in FIG. 4.
Figure 10:
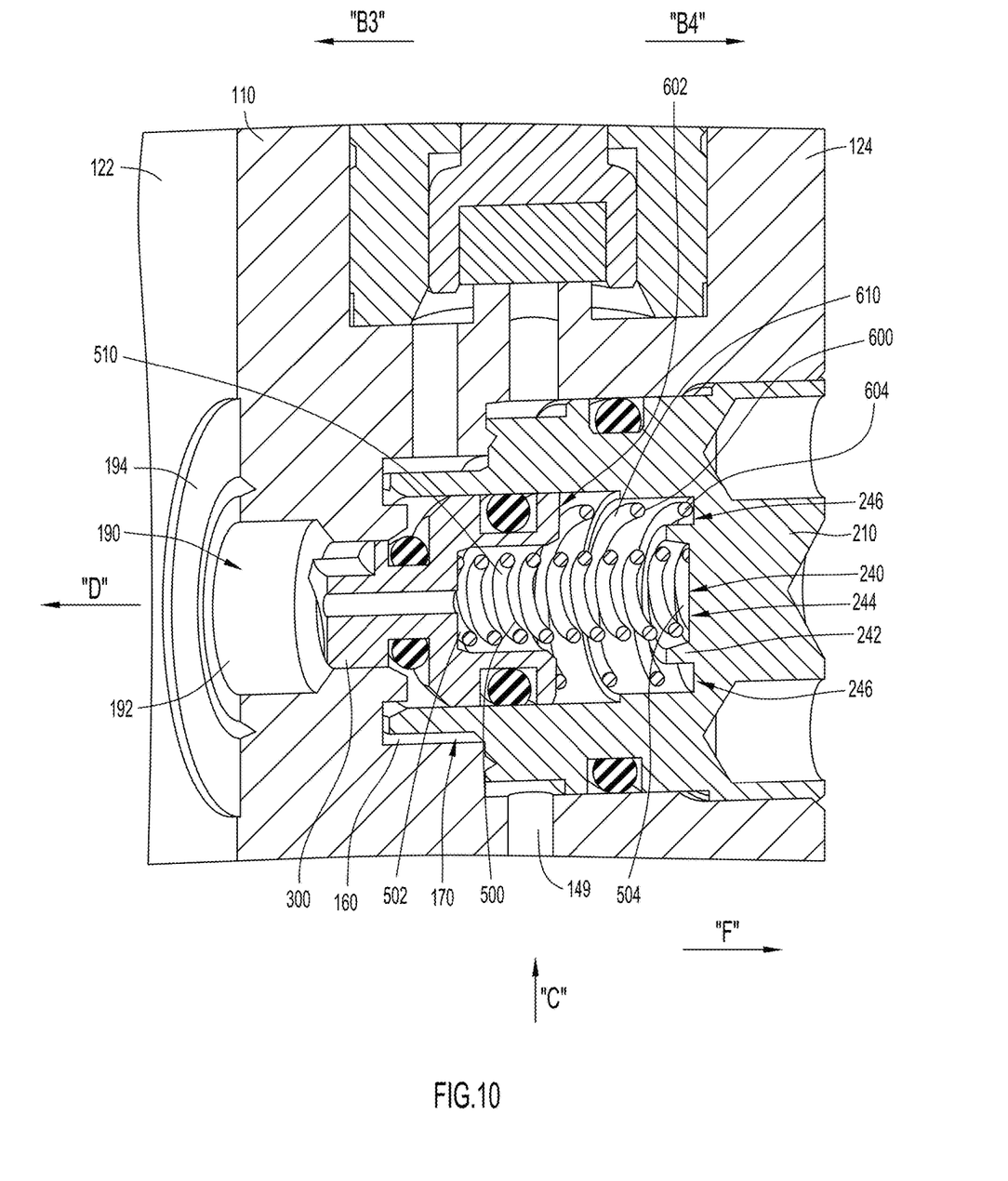
FIG. 10 is another close-up cross-sectional view of several components of the medical pin index valve illustrated in FIG. 4.

Turning to FIGS. 9 and 10, close-up cross-sectional views of several components of the medical pin index valve 100 are illustrated. The main body portion 120 of the valve body 110 includes outer side surfaces 122 and 124 on opposite sides thereof. The orientation of the components in FIG. 9 are in the opposite direction to the orientation illustrated in FIG. 6. Inlet passageway portion 149 has pressurized fluid flowing therethrough along the direction of arrow "C." The pressurized gas fills the cavity 170 and engages the sealing member 200, thereby applying a biasing force to member 200 along the direction of arrow "F." If the pressure of the gas in cavity 170 is sufficiently high, the gas moves the sealing member 200 to unseat it from the outlet 190. When the outlet 190 is opened, the pressurized gas can exit the valve body 110 through outlet 190 along the direction of arrow "D."

In this embodiment, the fixed member 200 includes a body or body portion 210 with an outer end 212 and an inner end 214. Proximate to outer end 212 is a locking portion 216 that engages a notch in the valve body 110 to secure the fixed member 200 in the cavity 170. The outer surface 220 of the fixed member 200 has a groove 222 formed therein in which O-Ring 224 is located.

In FIG. 9, the fixed member 200 includes inner wall portion 230 and inner wall portion 232, which collectively define a cavity 234 with two different portions. In this embodiment, the inner diameter of the portion of the cavity defined by inner wall portion 230 is larger than the inner diameter of the portion of the cavity defined by inner wall portion 232. The difference in diameters leads to a stepped inner wall for the cavity 234.

Referring to FIG. 10, the fixed member 200 includes an inner end surface 240, which with the inner wall portions 230 and 232, also defines the cavity 234 of the fixed member. Extending from the inner end surface 240 is an annular shoulder 242. Within the annular shoulder 242 is an inner portion 244 of the inner end surface 240. Outside of the annular shoulder 242 is an outer portion 246 of the inner end surface 240. The outer portion 246 extends around the outer perimeter of the annular shoulder 242.

Returning back to FIG. 9, the sealing member 300 includes a body 310, which is shown in its closed or sealing position 302. The body 310 has an outer end 312 and an opposite inner end 314. In this embodiment, the inner end 314 has an inner end surface 316 that is engaged by spring 600. That inner end surface 316 is a location for the nested biasing system to engage the sealing member 300.

The sealing member body 310 includes an outwardly extending flange portion 320 that has on one side a groove 322 for O-Ring 326 and on the other side a groove 324 for sealing member 328. As shown, O-Ring 326 engages an internal surface of the valve body 110, and the sealing member 328 engages inner wall portion 230 of the fixed member 200.

The body 310 also includes an inner side wall 330 and an inner end surface 340 that collectively define a cavity 350. The inner end surface 340 is engaged by spring 500 and forms another location for the nested biasing system to engage the sealing member 300.

The nested biasing system 400, which includes springs 500 and 600, is located between the fixed member 200 and the sealing member 300. The springs 500 and 600 apply biasing forces on the sealing member 300 along the direction of arrow "B3." Simultaneously, springs 500 and 600 apply biasing forces on the fixed member 200 along the direction of arrow "B4."

Turning to FIG. 10, spring 500 has a body 510 that extends to opposite ends 502 and 504. End 502 of spring 500 engages the sealing member 300 at location 342 on inner end surface 340. End 504 of spring 500 engages the fixed member 200 at the location of the inner portion 244 of the inner end surface 240 within the annular shoulder 242.

Spring 600 has a body 610 that extends to opposite ends 602 and 604. End 602 of spring 600 engages the sealing member 300 at location 318 on inner end surface 316. End 604 of spring 600 engages the fixed member 200 at the location of the outer portion 246 of the inner end surface 240 outside of the annual shoulder 242. As previously mentioned, the ends of the springs 500 and 600 engage the fixed member and the sealing member simultaneously, thereby allowing biasing forces "B3" and "B4" to be applied by springs 500 and 600.

The body of each of the springs 500 and 600 has an outer surface defining an outer diameter and an inner surface defining an inner diameter and a passage extending through the spring body. The nested arrangement shown in FIGS. 9 and 10 includes spring 500 extending through spring 600. The outer diameter of spring 500 is small enough that spring 500 fits within the cavity 330 of sealing member 300. The outer diameter of spring 600 is larger than the diameter of the cavity 300 so that spring 600 does not enter the cavity 330.

While this application has described the techniques presented herein in detail and with reference to specific embodiments thereof, it is nevertheless not intended to be limited to the details shown, since it will be apparent that various modifications and structural changes may be made therein without departing from the scope of the inventions and within the scope and range of equivalents of the claims. In addition, various features from one of the embodiments may be incorporated into another of the embodiments. Accordingly, it is appropriate that the appended claims be construed broadly and in a manner consistent with the scope of the disclosure as set forth in the following claims.

Finally, it is intended that the present invention cover the modifications and variations of this invention that come within the scope of the appended claims and their equivalents. For example, it is to be understood that terms such as "left," "right," "top," "bottom," "front," "rear," "side," "height," "length," "width," "upper," "lower," "interior," "exterior," "inner," "outer" and the like as may be used herein, merely describe points of reference and do not limit the present invention to any particular orientation or configuration. Further, the term "exemplary" is used herein to describe an example or illustration. Any embodiment described herein as exemplary is not to be construed as a preferred or advantageous embodiment, but rather as one example or illustration of a possible embodiment of the invention.

Similarly, when used herein, the term "comprises" and its derivations (such as "comprising", etc.) should not be understood in an excluding sense, that is, these terms should not be interpreted as excluding the possibility that what is described and defined may include further elements, steps, etc. Meanwhile, when used herein, the term "approximately" and terms of its family (such as "approximate", etc.) should be understood as indicating values very near to those which accompany the aforementioned term. That is to say, a deviation within reasonable limits from an exact value should be accepted, because a skilled person in the art will understand that such a deviation from the values indicated is inevitable due to measurement inaccuracies, etc. The same applies to the terms "about" and "around" and "substantially". Finally, for the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C).

What is claimed is:

1. A medical gas pin index valve, comprising:
a body defining an inlet passageway, a body cavity, and an outlet passageway, the cavity being in fluidic communication with each of the inlet passageway and the outlet passageway;
a fixed member coupled to the body, the fixed member being substantially located in the body cavity, the fixed member defining its own cavity; and
a sealing member located in the fixed member cavity, the sealing member being placeable in a sealed position and an opened position, the sealing member preventing a fluid from traveling from the inlet passageway to the outlet passageway when the sealing member is in its sealed position, the sealing member being biased toward its sealed position by a first spring and by a second spring, each of the first spring and the second spring engaging both the fixed member and the sealing member, the second spring being located inside of the first spring, wherein the first spring has a first length, the second spring has a second length, and the second length is greater than the first length.

2. The medical gas pin index valve of claim 1, wherein the sealing member moves to its sealed position when the pressure of a combined biasing force from the first spring and the second spring on the sealing member is greater than the pressure of the fluid in the inlet passageway.

3. The medical gas pin index valve of claim 1, wherein the fixed member includes an inner end surface, the first spring engages a first portion of the inner end surface, the second spring engages a second portion of the inner end surface, and the second portion of the inner end surface is separated from the first portion of the inner end surface by an annular shoulder.

4. The medical gas pin index valve of claim 3, wherein the first spring engages a third surface on the sealing member, the second spring engages a fourth surface on the sealing member, and the fourth surface is different from the third surface.

5. The medical gas pin index valve of claim 1, wherein the sealing member includes a body that has an end surface and a cavity that has an inner end surface, the first spring engages the sealing member body end surface, and the second spring engages the sealing member body inner end surface.

6. The medical gas pin index valve of claim 1, wherein the sealing member body cavity is defined by an inner wall having a first diameter, the first spring has a second diameter, the second spring has a third diameter, the third diameter is smaller than the first diameter, and the first diameter is smaller than the second diameter.

7. The medical gas pin index valve of claim 1, wherein the first spring has a first diameter, the second spring has a second diameter, the first diameter being greater than the second diameter, and each of the first spring and the second spring applies a simultaneous force on the sealing member to move the sealing member to its sealed position.

8. A medical gas pin index valve, comprising:
a body defining an inlet passageway and an outlet passageway, the body having a fixed member coupled thereto, the fixed member defining a first cavity;
a sealing member movably mounted in the body, a least a portion of the sealing member being located in the first cavity, the sealing member defining a second cavity, the sealing member being placeable in a sealed position in which a fluid is prevented from traveling from the inlet passageway to the outlet passageway, and an opened position in which a fluid can travel from the inlet passageway to the outlet passageway;
a first spring engaging the fixed member and the sealing member, the first spring biasing the sealing member toward its sealed position; and
a second spring engaging the fixed member and the sealing member, the second spring biasing the sealing member toward its sealed position, wherein the first spring applies a first biasing force at a first location on the sealing member, and the second spring applies a second biasing force at a second location on the sealing member, the second location being located inside of the first location, and the first spring has a first length, the second spring has a second length, and the second length is greater than the first length.

9. The medical gas pin index valve of claim 8, wherein a combination of the first biasing force and the second biasing force together moves the sealing member to its sealing position, thereby causing fluid having a residual pressure to remain in the inlet passageway.

10. The medical gas pin index valve of claim 9, wherein the residual pressure is in the range of 0.5 bar to 4 bar.

11. The medical gas pin index valve of claim 10, wherein the residual pressure is in the range of 3 bar to 4 bar.

12. The medical gas pin index valve of claim 8, wherein the second spring is located inside of the first spring.

13. The medical gas pin index valve of claim 8, wherein the first spring has a first diameter, the second spring has a second diameter, the first diameter is different than the second diameter.

14. The medical gas pin index valve of claim 13, wherein the first diameter is greater than the second diameter, and the first spring and the second spring have a nested arrangement.

15. A medical gas pin index valve, comprising:
a valve body defining an inlet passageway, a cavity, and an outlet passageway, the body having a fixed member coupled thereto and located in the cavity;
a sealing member movably mounted in the body, the sealing member being placeable in a sealed position in which a fluid is prevented from traveling from the inlet passageway to the outlet passageway, and an opened position in which a fluid can travel from the inlet passageway to the outlet passageway; and
a nested biasing system located between the fixed member and the sealing member, the nested biasing system applying a first biasing force on the sealing member at a first location and a second biasing force on the sealing member at a second location, each of the first biasing force and the second biasing force being applied to the sealing member along a same direction, wherein the sealing member moves to its sealed position when the combination of the first biasing force and the second biasing force is greater than a pressure of a fluid in the inlet passageway, and wherein the nested biasing system includes a first spring having a first length, a second spring having a second length, and the second length is greater than the first length.

16. The medical gas pin index valve of claim 15, wherein the
first spring engages the fixed member and the sealing member, the first spring applying the first biasing force; and
the second spring engages the fixed member and the sealing member, the second spring applying the second biasing force, the second location being different than the first location.

17. The medical gas pin index valve of claim 16, wherein the second spring is located inside of the first spring.

18. The medical gas pin index valve of claim 15, wherein the sealing member includes a body that defines a cavity and that has an end surface outside of the cavity, the second location is inside the sealing member cavity, and the first location is on the sealing member end surface.

19. The medical gas pin index valve of claim 15, wherein the biasing system applies a third biasing force on the fixed member in a second direction and a fourth biasing force on the sealing member on the fixed member in the second direction, and the third biasing force and the fourth biasing force are applied on the same surface of the fixed member.

* * * * *